United States Patent [19]

Switchenko et al.

[11] Patent Number: 5,272,054

[45] Date of Patent: Dec. 21, 1993

[54] ASSAY BY ENZYME-CATALYZED ISOTOPIC EXCHANGE

[75] Inventors: Arthur C. Switchenko, Sunnyvale; Edwin F. Ullman, Atherton, both of Calif.

[73] Assignee: Syntex (U.S.A.) Inc., Palo Alto, Calif.

[21] Appl. No.: 857,883

[22] Filed: Mar. 26, 1992

[51] Int. Cl.$^5$ .................... C12Q 1/00; G01N 33/567
[52] U.S. Cl. .................................. 435/4; 435/7.72; 435/7.9; 435/15; 435/26; 435/189; 435/191; 435/810; 435/814; 435/968; 435/975; 436/504; 436/542; 436/545; 436/804; 424/1.1
[58] Field of Search ............ 435/4, 7.72, 7.9, 15, 435/26, 189, 191, 810, 814, 968, 975; 436/504, 542, 545, 804; 424/1.1

[56] References Cited

U.S. PATENT DOCUMENTS

| | | | |
|---|---|---|---|
| 4,242,222 | 12/1980 | Johnson et al. | 252/301.17 |
| 4,242,456 | 12/1980 | Johnson et al. | 435/193 |
| 4,275,150 | 6/1981 | Vlachakis | 435/7 |
| 4,284,587 | 8/1981 | Johnson et al. | 564/365 |
| 4,287,368 | 9/1981 | Johnson et al. | 568/436 |
| 4,288,542 | 9/1981 | Johnson et al. | 435/15 |
| 4,311,790 | 1/1982 | Vlachakis | 435/15 |
| 4,591,551 | 5/1986 | DeQuattro et al. | 435/15 |
| 4,649,107 | 3/1987 | Bowsher et al. | 435/15 |
| 4,769,322 | 9/1988 | Henry et al. | 435/15 |

FOREIGN PATENT DOCUMENTS

DT 2062582  6/1972 Fed. Rep. of Germany.
DT 2717306 11/1977 Fed. Rep. of Germany.

OTHER PUBLICATIONS

Hung et al, *Biochem. Biophy. Res. Commun.*, vol. 46, No. 2, pp. 399–405, 1972.
Valera, V., et al., *Biochem. Biophy. Res. Commun.* Oct. 1987, vol. 148(1), 515–520.
Hussain, M. N., et al., *Clin. Chem.* 1985, vol. 31(11), 1861–1864.
Nagel-Hiemke, M., et al., *J. Biochem. Biophys. Meth.* 1981, vol. 4(5–6), 261–270.
Hussain, M. N., et al., *Anal. Biochemistry* 1981, vol. 111(1), 105–110.
Giulidori, P., et al., *Anal. Biochemistry* 1984, vol. 137(1), 217–220.
Harvima, R. J., et al., *Clinica Chimica Acta* 1988, vol. 171(2–3), 247–256.
Robison, L. R., et al., *Antimicrobial Agents and Chemotherapy*, 1978, vol. 13(1), 25–29.
Stevens, P., et al., *Antimicrobial Agents and Chemotherapy*, 1975, vol. 7(3), 374–376.
Chan, A., et al., *Life Sciences*, 1981, vol. 28(6), 697–703.
Consolo, S., et al., *Journal of Neurochemistry*, 1987, vol. 48(5), 1459–1465.
Kredich, N. M., et al., *Analytical Biochemistry*, 1981, vol. 116(2), 503–510.
Smith, D. H., et al., *N. England Journal Medicine*, 1972, vol. 286(11), 583–586.
Ipata, P. L., et al., *Anal. Biochemistry*, 1987, vol. 164(2), 411–417.
Brackman, Th., et al., *Anal. Biochemistry*, 1983, vol. 130(2), 369–375.
Schneider, P. B., *Journal of Lipid Research*, 1977, vol. 18(3), 396–399.
Neuberger, M. S., et al., *Biochem. Journal*, 1979, vol. 183, 31–42.

*Primary Examiner*—Michael G. Wityshyn
*Assistant Examiner*—Abdel A. Mohamed
*Attorney, Agent, or Firm*—Mark L. Bosse

[57] ABSTRACT

A method of assay for isotopically exchangeable analytes is disclosed. Analytes are labeled by enzymatic exchange of a hydrogen atom of the analyte and a deuterium or tritium atom. Preferably, analytes are labeled by reaction with an oxidant, a reducing agent which contains a deuterium or tritium atom, and an enzyme capable of catalyzing the reversible exchange of a hydrogen atom between the analyte, the oxidant, and the reducing agent. Kits for conveniently performing the assay methods are also disclosed.

50 Claims, No Drawings

ASSAY BY ENZYME-CATALYZED ISOTOPIC EXCHANGE

BACKGROUND OF THE INVENTION

1. Field of the Invention

Although many substances can be assayed by immunoassay, the method depends on the availability of high affinity and specificity antibodies. It is particularly difficult to obtain useful, highly specific antibodies to saccharides, particularly monosaccharides, and other substances, which are naturally present in body fluids, such as NADH, hydroxy acids, steroids, saturated and unsaturated fatty acids, etc. Methods of radioimmunoassay typically require radiolabeled analytes in addition to high affinity and specificity antibodies. Such radiolabeled analytes are frequently difficult or inconvenient to obtain.

Radioenzymatic assays utilize enzymes for the conversion of an analyte to a radiolabeled product. The radiolabel is typically derived from a radioactive enzyme cofactor such as S-adenosyl-L-[methyl-$^3$H]methionine, [$^{14}$C]ATP, [$^3$H]acetyl CoA, [$^{14}$C]acetyl CoA, [$^{14}$C]adenine, [$\gamma$=$^{32}$P]ATP, or [$^{14}$C]CTP. These assays frequently rely on (1) the transfer of a large radiolabeled group such as methyl, acetyl, nucleotide/nucleoside, or (2) phosphorylation.

A method of assay which eliminates the need for high affinity and specificity antibodies and/or radiolabeled analytes would be advantageous. The present invention relates to methods of assay which eliminate the need for both antibodies and radiolabeled analytes.

2. Brief Description of the Related Art

Preparation of isotopically labeled alcohols by exchange of hydrogen atoms for deuterium or tritium atoms has been reported. For example, Roth, C., German Patent No. 2062582 (1972) reports the preparation of stereospecific hydrogen isotope labeled alcohols by use of AND(P) dependent dehydrogenases.

Preparation of isotopically labeled NADH or NADPH has been reported. For example, Valera, V.; et al. *Biochem. Biophy. Res. Commun.* 1987, 148(1), 515-520 reports the preparation of 4R- and 4S-tritium labeled NADH and NADPH by use of glucose dehydrogenase from *Bacillus sp.*, alcohol dehydrogenase from *Thermoanaerobium brockii* and D-[1-$^3$H]glucose.

Enzymatic incorporation of a radiochemical label into an enzyme substrate or removal of a label from a substrate by enzyme catalysis has reportedly been used to study enzyme mechanisms. Further, microbial conversion of radiolabeled nutrients to a radioactive product, such as [$^{14}$C]CO$_2$, has reportedly been used to detect microorganisms.

Radioenzymatic assays involving methyl, acetyl, nucleotide, nucleoside, and phosphate group transfers have been reported.

Hussain, M. N.; et al. *Clin. Chem.* 1985, 31(11), 1861-1864 reports the use of catechol-O-methyltransferase (COMT) and S-adenosyl-L-[methyl-$^3$H]methionine ([$^3$H]SAM) in the analysis of dopamine, norepinephrine, and epinephrine.

Nagel-Hiemke, M.; et al. *J. Biochem. Biophys. Meth.* 1981, 4(5-6), 261-270 reports the use of COMT and [$^3$H]SAM in the analysis of dihydroxymandelic acid, dihydroxyphenylglycol, and dihydroxyphenylacetic acid.

Johnson, G. A.; et al. U.S. Pat. No. 4,288,542 (1981) reports the use of COMT and [$^3$H]SAM in the analysis of catecholamines.

Vlachakis, N. D. U.S. Pat. No. 4,311,790 (1982) reports the use of COMT and [$^3$H]SAM in the analysis of 3,4-dihydroxyphenylglycol.

Johnson, G. A.; et al. German Patent No. 2717306 (1977) and equivalent U.S. Pat. Nos. 4,242,222 (1980), 4,242,456 (1980), 4,284,587 (1981), and 4,287,368 (198) reports the use of COMT and [$^3$H]SAM in the analysis of epinephrine, norepinephrine, and dopamine.

Hussain, M. N.; et al. *Anal. Biochem.* 1981, 111(1), 105-110 reports the use of hydroxyindole-O-transferase (HIOMT) and ([$^3$H]SAM) in the analysis of indolealkylamines such as serotonin and acetylserotonin.

Giulidori, P.; et al. *Anal. Biochem.* 1984, 137(1), 217-220 reports the use of HIOMT and [$^3$H]SAM in the analysis of S-adenosyl-L-methionine (SAM).

Harvima, R. J.; et al. *Clin. Chim. Acta* 1988, 171(2-3), 247-256 and Henry, D. P.; et al. U.S. Pat. No. 4,769,322 (1988) describe the use of histamine-N-methyl- transferase (HNMT) and [$^3$H]SAM in the analysis of histamine.

Bowsher, R. R.; et al. U.S. Pat. No. 4,649,1077 (1987) reports the use of phenylethanolamine-N-methyl transferase (PNMT) and [$^3$H]SAM in the analysis of noradrenalin.

Vlachakis, N. D. U.S. Pat. No. 4,275,150 (1981) and De Quattro, V.; et al. U.S. Pat. No. 4,591,551 (1986) report the use of PNMT and [$^3$H]SAM in the analysis of normetanephrine and/or octopamine.

Robison, L. R.; et al. *Antimicrob. Agents Chemother.* 1978, 13(1), 25-29 reports the use of chloramphenicol acetyltransferase (CAT) and [$^{14}$C]acetyl Coenzyme A ([$^{14}$C]acetyl CoA) in the analysis of chloramphenicol.

Stevens, P.; et al. *Antimicrob. Agents Chemother.* 1975, 7(3), 374-376 reports the use of kanamycin acetyltransferase (KAT) and [$^3$H]acetyl Coenzyme A ([$^3$H]acetyl CoA) in the analysis of aminoglycosides such as amikacin, tobramycin, and sisomicin.

Chan, A.; et al. *Life Sci.* 1981, 28(6), 697-703 reports the use of acetyl CoA synthetase/serotonin-N-acetyl transferase (ACS/SNAT) and [$^3$H]acetate/tryptamine in the analysis of Coenzyme A.

Consolo, S.; et al. *J. Neurochem.* 1987, 48(5), 1459-1465 reports the use of acetyl-CoA:choline-O-acetyltransferase (ACCOAT) and [$^3$H]acetyl-CoA in the analysis of acetylcholine.

Kredich, N. M.; et al. *Anal. Biochem.* 1981, 116(2), 503-510 reports the use of S-adenosyl-L-homocysteine hydrolase (AHH) and [$^3$H]adenosine in the analysis of S-adenosyl-L-homocysteine and L-homocysteine.

Smith, D. H.; et al. *N. Engl. J. Med.* 1972, 286(11), 583-586 reports the use of gentamicin adenyl transferase (GAT) and [$^{14}$C]ATP in the analysis of aminoglycosides such as gentamicin.

Ipata, P. L.; et al. *Anal. Biochem.* 1987, 164(2), 411-417 reports the use of adenine phosphoribosyltransferase (APT) and [$^{14}$C]adenine in the analysis of 5-phosphorylribosyl-1-pyrophosphate.

Brackmann, Th.; et al. *Anal. Biochem.* 1983, 130(2), 369-375 reports the use of CMP-N-acetylneuraminic acid synthetase (CNAAS) and [$^{14}$C]CTP in the analysis of N-acetylsialic acid and CMP-N-acetylsialic acid.

Schneider, P. B. *J. Lioid Res.* 1977, 18(3), 396-399 reports the use of glycerol kinase (GK) and [$\gamma-^{32}$P]ATP in the analysis of glycerol and acylglycerol.

The purification and properties of *Klebsiella aeroegenes* D-arabinitol dehydrogenase has been reported by Neuberger, et al., in *Biochem. J.*, 183 (1979) 31–42.

SUMMARY OF THE INVENTION

One aspect of the present invention relates to methods for determining the presence or amount of an analyte in a sample suspected of containing the analyte. The analyte is capable of enzyme catalyzed reversible oxidation with exchange of a hydrogen atom. The methods involve the steps of: (1) treating the sample to enzymatically exchange a hydrogen atom of the analyte with a deuterium or tritium atom and (2) determining whether a hydrogen atom of the analyte has been exchanged with a deuterium or tritium atom. The occurrence of exchange indicates the presence or amount of the analyte in the sample.

In one embodiment, the treating step involves combining: (1) the sample, (2) an oxidant, (3) a reducing agent containing an isotope of hydrogen, usually a deuterium or tritium atom, and (4) one or more enzymes which individually or together are capable of exchanging a hydrogen atom of the analyte with an isotope of hydrogen, usually a deuterium or tritium atom of the reducing agent by catalyzing the reversible oxidation of the analyte. The reducing agent may be a reduced form of the oxidant that differs from the oxidant by at least the addition of an isotope of hydrogen, usually a deuterium or tritium atom.

The determining step can involve separating the reducing agent or the analyte from the sample. In one embodiment the separating step involves treating the sample with an agent capable of specifically binding the analyte. In one such embodiment the agent is attached to, or is capable of being attached to, a solid support or other means for separating it from sample. Alternatively, the determining step can be accomplished without separating the reducing agent from the sample, as for example, by use of spectroscopic means for determining the presence or amount of analyte having a hydrogen atom exchanged with an isotope of hydrogen, usually a deuterium or tritium atom.

Another aspect of the invention relates to methods for determining the presence or the amount of an analyte having a primary or secondary hydroxy group in a sample suspected of containing the analyte. The method involves the steps of: (a) combining in an assay medium: (1) the sample, (2) an oxidant, (3) a reduced form of the oxidant that differs from the oxidant by at least the addition of a deuterium or tritium atom, and (4) an enzyme capable of catalyzing the exchange of hydrogen isotopes between the analyte and the reduced form of the oxidant; (b) incubating the assay medium for a sufficient time to permit the above exchange; and (c) determining the amount of deuterium or tritium incorporated into the analyte. The amount of incorporated deuterium or tritium indicates the presence or amount of the analyte in the sample.

Another aspect of the invention relates to improved methods for determining the presence or amount of an analyte capable of undergoing hydrogen exchange catalyzed by an oxidoreductase enzyme in a sample suspected of containing the analyte. The improvement of this aspect of the invention involves the steps of: (1) combining in a medium: (a) the sample, (b) a hydrogen isotope-enriched compound capable of transferring the hydrogen isotope into the analyte as a result of the action of the enzyme on the analyte; and (2) detecting the analyte having the hydrogen isotope.

The detecting step can involve separating the compound from the analyte. In one embodiment the separating step involves treating the medium with an agent capable of binding the compound. In one such embodiment the agent is attached to, or is capable of being attached to, a solid support or other means for separating it from the analyte. Alternatively, the separating step can involve treating the medium with an agent capable of binding the analyte. In one such embodiment the agent is attached to, or is capable of being attached to, a solid support or other means for separating it from the compound. Alternatively, the detecting step can be accomplished without separating the compound from the medium, as for example, by use of spectroscopic means for detecting the presence or amount of analyte having a hydrogen atom exchanged with an isotope of hydrogen, usually a deuterium or tritium atom.

The assay methods of the present invention are useful for determining the presence or amount of an analyte capable of enzyme catalyzed reversible oxidation with exchange of a hydrogen atom without high affinity and specificity antibodies to the analyte of interest and/or without radiolabeled analyte.

Another aspect of the invention relates to kits which include in packaged combination reagents and materials used in the assay methods of the invention. Such kits are useful for conveniently performing the assay methods of the invention.

DESCRIPTION OF THE SPECIFIC EMBODIMENTS

The present invention relates to methods for determining the presence or amount of an analyte capable of enzyme catalyzed reversible oxidation in which at least one hydrogen atom of the analyte is exchanged with a hydrogen isotope, usually a deuterium or tritium atom. The methods require that the oxidation reaction be reversible, preferably, but not mandatorily, under the same reaction conditions as the oxidation reaction. In the methods, a sample suspected of containing an analyte is combined with a hydrogen isotope labeled reagent, usually a reducing agent and one or more enzymes capable of reversibly oxidizing the analyte with transfer of the hydrogen isotope of the labeled reagent to the analyte. By determining the amount of exchange, the presence or amount of the analyte can be determined.

Scheme I

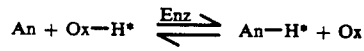

A reversible enzymatic oxidation of an analyte having an enzymatically exchangeable hydrogen atom (An-H) by action of an enzyme catalyst (Enz), an oxidant (Ox), a reducing agent (Ox-H) and an isotopically labeled reducing agent (Ox-H*) is shown in Scheme I. The analyte (An-H) is reversibly converted to its oxidized form (An), which in turn is reversibly reduced to form isotopically labeled analyte (An-H*).

The system depicted in Scheme I involves a single enzyme (Enz). Systems involving multiple enzymes and systems in which multiple oxidations occur are contemplated within the scope of the present invention. Such a system is depicted in Scheme II.

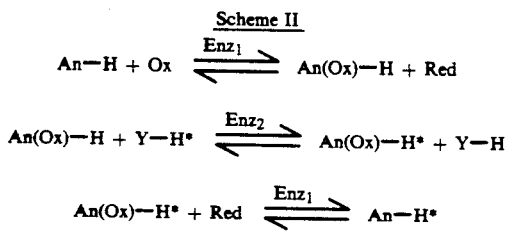

Scheme II

In such a system the analyte (An-H) can be oxidized to an intermediate (An(Ox)-H) by oxidant (Ox). The intermediate in turn undergoes an enzyme catalyzed exchange reaction with a labeled reagent (Y-H*) to form isotopically labeled intermediate (An(Ox)-H*) and unlabelled reagent (Y-H). The labeled intermediate (An(Ox)-H*) is then converted to labeled analyte (An-H*) by the reduced form of the oxidant (Red).

In one embodiment of the invention an assay for an analyte having an enzymatically exchangeable hydrogen atom (An-H) can be performed by: (1) combining a medium suspected of containing the analyte (An-H), an oxidant (Ox), a hydrogen isotope labeled reducing agent (Ox-H*), and one or more enzymes (Enz) capable of catalyzing the reversible oxidation of the analyte (An-H); and (2) determining whether a hydrogen atom (H) of the analyte (An-H) has been exchanged with a hydrogen isotope (H*) to form an analyte derivative in which a hydrogen atom (H) has been exchanged with a hydrogen isotope (An-H*).

In the determining step, the occurrence of exchange of at least one hydrogen atom (H) of the analyte (An-H) with a hydrogen isotope (H*) to form analyte having a hydrogen atom exchanged with a hydrogen isotope (An-H*) indicates the presence or amount of the analyte (An-H) in the medium suspected of containing the analyte (An-H).

Before describing the detailed embodiments of the invention, a number of terms will be defined.

DEFINITIONS

The term "determining the presence or amount of an analyte" includes qualitative, semi-quantitative and quantitative methods for determining an analyte. Such methods can provide one or more detectable responses to the presence or amount of analyte. Such methods can also provide one or more detectable responses in the absence of analyte.

The term "sample suspected of containing an analyte" includes any sample reasonably suspected of containing an analyte of interest. Such samples can include natural samples such as human or animal fluids or tissues. The term sample also includes man-made samples such as analyte separated from a natural sample such as by pretreatment or extraction process. Such a man-made sample may contain analyte and other constituents of the natural sample from which it was obtained usually in a diluent such as a pretreatment or extraction medium. The sample can be prepared in any convenient assay medium which does not interfere with the assay. Typically the sample is a natural sample such as whole blood, serum, plasma, saliva, sweat, tears, urine, bile, semen, cerebrospinal fluid or the like, which may be pretreated or used untreated, and may be prepared in an aqueous solution or used directly. Preferably, the enzyme which is employed in the methods of the invention, or other enzymes with like activity, will not be present in the sample suspected of containing the analyte, or will be removed or deactivated prior to the addition of the various assay reagents. Further, the sample suspected of containing the analyte is preferably free of naturally occurring inhibitors for the enzyme of the present invention, or such inhibitors should be removed or deactivated prior to the addition of the enzyme.

The term "agent capable of binding" includes a compound capable of binding another, for example by having an area on its surface or in a cavity which specifically binds to a particular spatial and polar organization of the other molecule. Such as for example a receptor, antibody, lectin, polynucleotide, synthetic receptor, and the like. Also included are small molecules which have specific chemical affinity for a particular compound or class of compounds such as acylhydrazides that bind aldehydes and ketones, alkyl and aryl boronates that bind vicinal glycols, aryl mercury compounds that bind mercaptans, ion exchange resins that bind polyanions, and the like. In the context of the present invention, an agent capable of binding will include agents capable of binding the analyte and agents capable of binding a hydrogen isotope labeled reagent.

The term "enzymatic exchange of at least one hydrogen atom of an analyte with an isotope of hydrogen, usually a deuterium or tritium atom" means that, apart from any other changes to the analyte, at least one hydrogen atom of the analyte is exchanged with an isotope of hydrogen directly or indirectly by action of at least one enzyme together with any necessary enzyme cofactors. Within the context of the present invention, exchange of at least one hydrogen atom with an isotope of hydrogen does not include exchange of a larger group which coincidentally contains a hydrogen atom. The enzymatic exchange of the present invention relates to enzymatic exchange of a hydrogen atom with an isotope of hydrogen, not to the exchange of multiatom groups containing an isotope of hydrogen.

SPECIFIC EMBODIMENTS

One aspect of the invention relates to methods for determining the presence or amount of an analyte capable of enzyme catalyzed reversible oxidation with exchange of a hydrogen atom in a sample suspected of containing the analyte. The method involves the steps of: (1) treating the sample to enzymatically exchange a hydrogen atom of the analyte with an isotope of hydrogen, preferably a deuterium or tritium atom, and (2) determining whether a hydrogen atom of the analyte has been exchanged with a hydrogen isotope, preferably a deuterium or tritium atom. The occurrence of exchange indicates the presence or amount of the analyte in the sample.

The analytes suitable for assay by the methods of the present invention depend on the availability of an enzyme or enzymes that can catalyze reversible oxidation resulting in replacement of a hydrogen atom of the analyte with an isotope of hydrogen, usually a deuterium or tritium atom. Preferably, such enzymes are specific for the desired reversible oxidation reaction of the desired analyte and do not substantially catalyze other hydrogen isotope exchange reactions of components in the sample or assay medium. Any analyte for which such an enzyme exists or can be prepared is suitable for use in the methods of the present invention.

Usually, the analyte will contain a primary or secondary hydroxy group. The method is useful for analytes such as saccharides, steroids, glycolipids, prostaglandins, toxins, amino acids, and the like, that contain a primary or secondary hydroxy group. Preferred steroid analytes include particularly the androgenic steroids, as well as cholesterol, estradiol, estriol, and the like. An exemplary toxin is tetrodotoxin. Amino acids having a primary or secondary hydroxy group include serine, homoserine, threonine, and unnatural amino acids.

Within the context of the invention, saccharides are preferred analytes. Particularly preferred saccharide analytes are monosaccharides such as arabinitol, lactate, mannitol, glucose, gluconic acid, galactose, glycerol, ribitol, xylitol, and the like. Among the most preferred analytes contemplated within the scope of the present invention is the monosaccharide D-arabinitol.

Enzymes suitable for use in the methods of the present invention are those enzymes capable of selectively catalyzing the reversible oxidation of the desired analyte wherein a hydrogen atom of the analyte is exchanged with an isotope of hydrogen, usually a deuterium or tritium atom. Such enzymes can be obtained in a number of ways. For example, the enzymes of the invention can be natural substances isolated from living organisms, natural substances expressed in other than their natural organism through genetic engineering technology, modified natural substances obtained in any way, or wholly man made substances.

Principles and techniques of enzyme isolation and purification have been described in detail elsewhere. Exemplary reports include Jakoby, W. B., ed. *Methods in Enzymology*, 1971, 22, "Enzyme Purification and Related Techniques"; Jakoby, W. B.; Wilchek, M., ed.s *Methods in Enzymology*, 1974, 34, "Affinity Techniques, Enzyme Purification Part B"; Jakoby, W. B., ed. *Methods in Enzymology*, 1984, 104, "Enzyme Purification and Related Techniques, Part C"; and Deutscher, M. P., ed. *Methods in Enzymology*, 1990, 182, "Guide to Protein Purification"; each of which is incorporated herein by reference in its entirety.

An example, by way of illustration and not limitation, of the isolation and purification of enzymes suitable for use in the methods of the present invention follows: Cells capable of producing a useful enzyme (for example D-arabinitol dehydrogenase (DADH) from *Candida tropicalis*) are cultivated in a liquid nutrient medium. Frequently, the medium contains the analyte as well as nitrogen, vitamins, trace metals, and the like, required by the organism. The cells are grown to late log phase at room temperature on a gyrotary shaker. The cells are then harvested, washed, pelleted and resuspended in a suitable buffer containing the appropriate proteinase inhibitors. The cells are then disrupted. Yeast cells are usually subjected to mechanical breakage such as a high speed vibrating bead mill or high pressure shearing, which is accomplished with, for example, a French pressure cell. Bacterial cells may be disrupted enzymatically (e.g., lysozyme), with ultrasound, or by the two methods described above. The resultant cell suspension is then subjected to centrifugation(s) that pellet unbroken cells, cell wall material and possibly membranes and ribosomes. The supernatant is then treated with highly positively charged polymers such as protamine sulfate, which will selectively precipitate nucleic acids and their associated proteins. The enzyme is then precipitated from the solution with a salt (e.g., ammonium sulfate), organic solvent (e.g., acetone), or organic polymer (e.g., polyethylene glycol). Final purification of the enzyme may be carried out using standard techniques such as ion exchange chromatography, reverse-phase chromatography, gel exclusion chromatography, gel electrophoresis, isoelectricfocusing, immunoaffinity chromatography, dye ligand chromatography, and the like.

An enzyme in accordance with the present invention can also be prepared by recombinant DNA technology (also referred to as genetic engineering technology and by other common synonyms). Briefly, a gene coding for the desired enzyme of the invention is obtained, usually by isolation from genetic matter of the organism from which the enzyme was isolated. Generally, the gene is isolated by partial digestion of the DNA followed by centrifugation through a gradient material such as sucrose. Gene fragments are cloned into a suitable cloning vector such as, for example, a plasmid, which is transfected into a host such as, for example, a bacterium, e.g., *Escherichia coli*.

Alternatively, the vector may be other than a plasmid, for example, bacteriophage or cosmid. The particular vector chosen should be compatible with the contemplated host, whether a bacterium such as *E. coli*, yeast, or other cell. The plasmid should have the proper origin of replication for the particular host cell to be employed. Also, the plasmid should impart a phenotypic property that will enable the transformed host cells to be readily identified from cells that do not undergo transformation. Such phenotypic characteristics can include genes providing resistance to growth inhibiting substances, such as an antibiotic. Plasmids are commercially available that encode proteins responsible for resistance to antibiotics, including tetracycline, streptomycin, sulfa drugs, penicillin and ampicillin. Similar characteristics will be considered for choosing vectors other than plasmids, such as the existence of a phenotypic marker and suitable restriction sites that allow the ligation of foreign genes.

The host cells carrying the gene are selected and gene expression is monitored. If expression is low, the synthesis of the enzyme in the bacteria may be improved by providing a suitable promoter at the 5'-end of the gene. Such promoters are found in commercially available expression plasmids. Once the gene has been expressed to appropriate levels, the protein is extracted from the bacterium. The enzyme is separated from other proteins by procedures described above.

A preferred way of screening cultures of naturally occurring or genetically manipulated organisms to determine whether an enzyme, in accordance with the invention, is obtained is to utilize a monoclonal antibody that specifically recognizes the enzyme. Generally, the binding of the enzyme to such a monoclonal antibody will be such that the binding affinity is greater than $10^6 \, M^{-1}$, preferably greater than $10^7 \, M^{-1}$, more preferably greater than $10^8 \, M^{-1}$.

Monoclonal antibodies for this purpose may be prepared by standard hybrid cell technology based on that reported by Kohler and Milstein in *Nature*, 1975, 256, 495–497. Briefly, a host is immunized with the specific enzyme or an immunologically active derivative or conjugate thereof. The enzyme (for example, the enzyme isolated as described above from *Candida tropicalis*) is injected into the host, usually a mouse or other suitable animal, and after a suitable period of time the spleen cells from the mouse are obtained. Alternatively, unsensitized cells from the host can be isolated and directly sensitized with the enzyme isolate in vitro. Hybrid cells are formed by fusing the above cells with an appropriate myeloma cell line and cultured. The antibodies produced by the cultured hybrid cells are screened for their binding affinity to the enzyme. A number of screening techniques may be employed such as, for example, ELISA screens including forward and reverse ELISA assays where a tracer enzyme such as a peroxidase or phosphatase is used. The screening assays can alternatively be conducted by measuring the activity of the antigenic enzyme where the antibodies are bound to a surface and the antigenic enzyme is used to contact the surface, washed away, and the residual activity measured as and indicator of the presence of antibody.

In the forward assay, the antigenic enzyme is provided on a suitable surface such as a microtiter plate. Supernatants from each of the hybrid colonies are individually applied to separate microtiter plate wells. After incubation, the wells are washed and goat antimouse antibodies covalently linked to alkaline phosphatase are added to each of the wells. The wells are again incubated and washed and then filled with a substrate for the phosphatase, such as, for example, p-nitrophenyl phosphate. The wells are then observed for a signal, which indicates the presence of an antibody specific for the enzyme. Hybrid cells so identified may be grown in culture, as an ascites tumor in mice or recloned to select for the hybrid cells that secrete a homogeneous population of antibodies specific for enzyme prior to further culture. The monoclonal antibodies may then be isolated from the culture medium or ascites fluid by standard techniques such as ion exchange or affinity chromatography.

In the reverse assay the microtiter plate well is coated with rabbit antimouse antibodies. A supernatant from each of the hybrid cell colonies is applied to separate wells. The wells are incubated and washed, and the antigenic enzyme preparation is added. After again incubating and washing, polyclonal antibody to the antigenic enzyme is added where this antibody is labeled with a tracer enzyme such as alkaline phosphatase. After another incubation and wash, the wells are screened for enzyme activity. The hybrid cells of positive wells are selected and may be grown in culture, as an ascites tumor in mice or recloned to select for the hybrid cells that secrete a homogeneous population of antibodies specific for enzyme prior to further culture. The monoclonal antibodies may then be isolated from the culture medium or ascites fluid by standard techniques such as ion exchange or affinity chromatography.

The monoclonal antibodies may also be prepared by cloning and expressing nucleotide sequences or mutagenized versions thereof coding at least for the amino acid sequences required for specific binding of natural antibodies.

Monoclonal antibodies may include a complete immunoglobulin, or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like.

As mentioned above, the monoclonal antibodies prepared in accordance with the above may be utilized in assays to screen enzyme preparations isolated from different organisms to obtain and identify the enzymes useful in the methods of the present invention. Illustrative monoclonal antibodies useful for obtaining and identifying a D-arabinitol dehydrogenase enzyme are recited in Table 3 hereinbelow.

As set forth above, enzymes suitable for use in the methods of the invention are those enzymes capable of catalyzing the reversible oxidation of the desired analyte wherein a hydrogen atom of the analyte is exchanged with an isotope of hydrogen, usually a deuterium or tritium atom. Preferably, the enzymes are selective for the desired reversible oxidation reaction of the target analyte. Such useful enzymes vary widely in their substrates, cofactors, specificity, natural abundance, temperature stability, optimum pH, turnover rate, and the like. Other than inherent factors, there are also the practical considerations, such as the extent that the enzyme has been characterized, the stability of the enzyme, its selectivity for the analyte of interest, its compatibility with the sample, ease of purification, and whether the enzyme is commercially available or readily prepared. As a practical matter, in choosing an enzyme for commercialization, as compared to a single or limited use for scientific investigation, there will be a number of desirable criteria. Preferably the enzyme should be sufficiently stable so as not to change activity during the course of the assay so as to interfere with the assay results and should be capable of being stored for a period of at least three months, and preferably at least 6–12 months at 2°–12° C. or above.

Although specific activity is not a critical factor, useful enzymes will usually have turnover rates of at least 5 international units/mg (IU/mg), usually at least 50 IU/mg and preferably at least 100 IU/mg. Of critical importance is that the enzyme be specific with respect to the analyte of interest and not catalyze the reversible oxidation of other substances in the sample or assay medium, other than cofactors. When a highly specific enzyme is not used, any non-analyte substances that are reversibly oxidized with hydrogen isotope incorporation must be readily separable from the analyte of interest. Preferably, the enzyme will be highly specific under the assay conditions and catalyze the oxidation of substances other than the analyte and cofactors less than 10% as fast, preferably less than 1% as fast as the analyte. Additionally the enzyme must be substantially free of other enzymes that could oxidize substances other than the analyte and cofactors with resultant exchange of hydrogen isotope wherein any such contaminating enzyme will preferably produce less than 10%, preferably less than 1% of the rate of hydrogen isotope exchange as occurs by catalyzed exchange of the analyte.

From the standpoint of operability, a wide variety of enzymes can be used in the methods of the invention. Illustrative lists of such enzymes including substrates, cofactors and natural sources are provided in *Enzyme Nomenclature*, Edwin C. Webb, ed., Academic Press, New York (1984) at pages 20–474 (hereinafter referred to as Webb); *Enzymes*, Malcolm Dixon, et al., Third Edition, Academic Press, New York (1979) at pages 683–972 (hereinafter referred to as Dixon); *Enzyme Handbook*, Vol. I, II, and Supp. I, Thomas E. Barman, Springer-Verlag, New York (1969) at pages 23–499, 501–915, and 16–503 respectively (hereinafter referred to as Barman); and *Enzyme Handbook*, Vol. 1 and 2, D. Schomburg and M. Salzmann, ed.s, Springer-Verlag, New York (1990) pages not numbered.

Further illustrative lists of enzyme systems applicable to carbohydrates are reported in Wood, W. A., ed., *Methods in Enzymology*, 1967, 9, "Carbohydrate Metabolism"; Wood, W. A., ed., *Methods in Enzymology*, 1975, 41, "Carbohydrate Metabolism, Part B"; Wood, W. A., ed., *Methods in Enzymology*, 1975, 42, "Carbohydrate Metabolism, Part C"; Wood, W. A., ed., *Methods in Enzymology*, 1982, 89, "Carbohydrate Metabolism, Part D"; and Wood, W. A., ed., *Methods in Enzymology*, 1982, 90, "Carbohydrate Metabolism, Part E". Exemplary enzymes include D-arabinitol dehydrogenase (I.U.B. class 1.1.1.11), D-lactate dehydrogenase (I.U.B. class 1.1.1.28), fructuronate reductase (also known as D-mannonate dehydrogenase, I.U.B. class 1.1.1.57), and glycerol dehydrogenase (I.U.B. class 1.1.1.72).

Further illustrative lists of enzyme systems applicable to lipids are reported in Lowenstein, J. M., ed., *Methods in Enzymology*, 1969, 14, "Lipids"; Lowenstein, J. M., ed., *Methods in Enzymology*, 1975, 35, "Lipids, Part B"; Lowenstein, J. M., ed., *Methods in Enzymology*, 1981, 71, "Lipids, Part C"; and Lowenstein, J. M., ed., *Methods in Enzymology*, 1981, 72, "Lipids, Part D". Exemplary enzymes include 4-hydroxybutyrate dehydrogenase (I.U.B. class 1.1.1.61) and ω-hydroxydecanoate dehydrogenase (I.U.B. class 1.1.1.66).

Further illustrative lists of enzyme systems applicable to steroids and terpenoids are reported in Clayton, R. B., ed., *Methods in Enzymology*, 1969, 15, ""Steroids and Terpenoids"; Law, J. H.; Rilling, H. C., ed.s, *Methods in Enzymology*, 1985, 111, "Steroids and Isoprenoids, Part A"; and Law, J. H.; Rilling, H. C., ed.s, *Methods in Enzymology*, 1985, 111, "Steroids and Isoprenoids, Part B." Exemplary enzymes include oestradiol 17-β-dehydrogenase (I.U.B. class 1.1.1.62) and 21-hydroxysteroid dehydrogenase (I.U.B. class 1.1.1.151).

Further illustrative lists of enzyme systems applicable to prostaglandins are reported in Smith, W. L., ed., *Methods in Enzymology*, 1982, 86, "Prostaglandins and Arachidonate Metabolites". Exemplary enzymes include 9-hydroxyprostaglandin dehydrogenase, and 15-hydroxyprostaglandin dehydrogenase (I.U.B. class 1.1.1.141).

Further illustrative lists of enzyme systems applicable to amino acids are reported in Colowick, S. P.; and Kaplan, N. O., ed.s, *Methods in Enzymology*, 1962, 5, "Preparation and Assay of Enzymes"; Tabor, H.; and Tabor, C. W., ed.s, *Methods in Enzymology*, 1970, vol. 17, Part A, "Metabolism of Amino Acids and Amines"; and Tabor, H.; and Tabor, C. W., ed.s, *Methods in Enzymology*, 1971, vol. 17, part B, "Metabolism of Amino Acids and Amines". Exemplary enzymes include homoserine dehydrogenase (I.U.B. class 1.1.1.3).

Among the enzymes useful in the methods of the invention, those classified by the International Union of Biochemistry (I.U.B.) as oxidoreductases (I.U.B. class 1) are preferred. Particularly preferred oxidoreductases are those in I.U.B. class 1.1 which act on a primary or secondary hydroxy group (a CHOH group). Among the oxidoreductases, those which use nicotinamide adenine dinucleotide (abbreviated herein as AND without regard to oxidation state or charge, the structure and an extensive list of synonyms can be found in *The Merck Index*. 11th Edition, Merck & Co., Rahway, N.J. (1989) at monograph number 6259, page 1002) or nicotinamide adenine dinucleotide phosphate (abbreviated herein as NADP or AND(P) without regard to oxidation state or charge, the structure and an extensive list of synonyms can be found in *The Merck Index*, 11th Edition, Merck & Co., Rahway, N.J. (1989) at monograph number 6262, page 1003) are further preferred. These AND or NADP dependent oxidoreductases fall into I.U.B. class 1.1.1 if they act on primary or secondary hydroxy groups.

As described above, particularly preferred analytes are saccharides, steroids, lipids, prostaglandins, toxins, and the like, which contain a primary or secondary hydroxy group. Consequently, more particularly preferred oxidoreductases are those which act on the primary or secondary hydroxy group of saccharides, steroids, lipids, prostaglandins, toxins, and the like. Similarly, because saccharides are an especially preferred class of analytes, oxidoreductases which act on the primary or secondary hydroxy group of saccharides are especially preferred.

Accordingly, enzymes contemplated within the scope of the invention as preferred are those of I.U.B. class 1.1.1. By way of illustration and not limitation, a list of enzymes from I.U.B. class 1.1.1. capable of reversibly oxidizing a wide range of substrates together with substrates, cofactors and oxidation products is set forth below as Table 1. Further listings of illustrative enzymes of I.U.B. class 1.1.1. can be found in Webb at pages 20–49; Dixon at pages 684–702; Barman Vol. I at pages 23–105; and Barman Supp. I at pages 16–66; the recited pages of each are incorporated herein by reference. Among the most preferred enzymes contemplated within the scope of the present invention are those AND or NADP dependent oxidoreductases which act on the primary or secondary hydroxy group of monosaccharides. Exemplary of these most preferred enzymes is D-arabinitol dehydrogenase (DADH).

TABLE 1

| IUB no. | Name | Substrate Oxidant/Reducing agent Oxidation product |
|---|---|---|
| 1.1.1.3 | Homoserine d.[1] | L-homoserine NAD(P)$^+$/NAD(P)H L-aspartate 4-semialdehyde |
| 1.1.1.28 | D-Lactate d. | (R)-lactate NAD$^+$/NADH pyruvate |
| 1.1.1.57 | Fructuronate r.[2] | D-mannonate NAD$^+$/NADH D-fructuronate |
| 1.1.1.62 | Estradiol 17β- d. | estradiol-17β NAD(P)$^+$/NAD(P)H estrone |
| 1.1.1.66 | ω-Hydroxy-decanoate d. | 10-hydroxydecanoate NAD$^+$/NADH 10-oxodecanoate |
| 1.1.1.72 | Glycerol d. | glycerol NAD(P)$^+$/NAD(P)H D-glyceraldehyde |
| 1.1.1.141 | 15-Hydroxy-prostaglandin d. | (15Z,13E)-(15S)-11α,15-dihydroxy-9-oxoprost-13-enoate NAD$^+$/NADH (15Z,13E)-11α-hydroxy-9,15-dioxoprost-13-enoate |
| 1.1.1.151 | 21-Hydroxysteroid d. | 21-hydroxycorticosteroid NAD$^+$/NADH 21-dehydrocorticosteroid |

[1] d. = dehydrogenase
[2] r. = reductase

The oxidants and reducing agents of the invention must be capable of functioning together with the enzyme(s) of the invention in a reversible oxidation reaction of the analyte such that at least one hydrogen atom of the analyte is exchanged with an isotope of hydrogen, usually a deuterium or tritium atom. The reducing agents must be further capable of being prepared or obtained with at least one isotopic atom, usually a deuterium or tritium atom available for exchange with at least one hydrogen atom of the analyte.

Preferred oxidants include AND, NADP and riboflavine derivatives such as flavine mononucleotide (FMN, riboflavine-5-phosphate) and flavine-adenine dinucleotide (FAD). Particularly preferred oxidants are AND, NADP and FMN. More particularly preferred oxidants are the nicotinamide adenine dinucleotides NAD and NADP. Among the most preferred oxidants contemplated within the scope of the present invention is NAD.

It is preferred that the reducing agent be a reduced form of the oxidant such that the reducing agent has at least one isotopic atom, usually a deuterium or tritium atom capable of exchange with at least one hydrogen atom of the analyte. In this embodiment, the reducing agent will differ from the oxidant by at least the addition of an isotope of hydrogen, usually a deuterium or tritium atom.

A further consideration in selecting a reducing agent is whether or not the reducing agent can be easily separated from fractions of the sample or assay medium suspected of containing the analyte. In some assay embodiments, it may be desirable to perform such a separation at some point during the assay.

It is contemplated within the scope of the invention that the reducing agent can have more than one isotopic atom, usually a deuterium or tritium atom. For example, some of the deuterium or tritium atoms contained in the reducing agent may be unavailable for exchange with a hydrogen atom of a particular analyte through the action of a particular enzyme. For example, certain enzyme/analyte combinations may result in the exchange of one of two asymmetrically disposed (pro-R or pro-S) deuterium or tritium atoms of a given reducing agent. As long as at least one of the deuterium or tritium atoms of the reducing agent are available for exchange with a hydrogen atom of the analyte, such unavailable deuterium or tritium atoms will not impede the use of the methods of the invention for the assay of the analyte.

It is also contemplated that the reducing agent will often have less than 100% of its exchangeable hydrogen atoms in the form of an isotopic atom, usually a deuterium or tritium atom. When the exchangeable atom is deuterium, the percentage of exchangeable hydrogen present as deuterium will preferably greater than 50%, more preferably greater than 70%, still more preferably greater than 90%. When the exchangeable atom is tritium, the percentage of exchangeable hydrogens present as tritium need only be sufficient to give a measurable signal and will frequently be less than 50%, usually less than 5% and may be 0.5% or less.

In view of the factors set forth above, preferred reducing agents include deuterated or tritiated NADH, NADPH and reduced riboflavine derivatives such as FMNH and FADH$_2$. Particularly preferred reducing agents are NADH, NADPH and FMNH. More particularly preferred reducing agents are the deuterated or tritiated nicotinamide adenine dinucleotide derivatives NADH and NADPH. Among the most preferred reducing agents contemplated within the scope of the present invention is deuterated or tritiated NADH.

Although the isotopically substituted reducing agent will normally be used directly as a component of the assay mixture, it may also be generated in situ during the course of the assay. Conveniently this can be done by including a primary or secondary alcohol having hydrogen isotope substitution at the carbon bearing the hydroxy group where the alcohol is capable of reducing the oxidant, usually by means of enzymic catalysis. Thus for example, isotopically substituted NADH can be formed from isotopically substituted lactate, NAD, and lactate dehydrogenase and isotopically substituted NADPH can be formed from isotopically substituted glucose-6-phosphate, NADP, and mammalian G6PDH.

A preferred method of selecting enzymes, oxidants and reducing agents useful in the methods of the invention involves the sequential steps of: (1) selecting an enzyme or enzymes capable of catalyzing the reversible oxidation of the desired analyte wherein a hydrogen atom of the analyte is exchanged with an isotope of hydrogen, usually a deuterium or tritium atom; and (2) selecting oxidants and reducing agents capable of functioning together with the enzyme or enzymes such that an isotope of hydrogen, usually a deuterium or tritium atom of the reducing agent is exchanged for a hydrogen atom of the analyte. By way of illustration and not limitation, the discussion and material incorporated by reference above describe exemplary sources of such suitable enzymes together with oxidants and reducing agents capable of functioning in the methods of the invention.

The assay will normally be carried out in an aqueous buffered medium at a moderate pH, generally that which provides optimum assay sensitivity. The assay can be performed directly on a sample of interest such as serum, urine, saliva, water sample, or the like, or the suspected analyte can be partially or completely separated prior to carrying out the assay. Additionally the analyte may be separated from the assay mixture following isotopic exchange or detected without separation.

It may be desirable or preferable to pretreat a sample to be assayed prior to conducting an assay in order to remove interferents, solubilize the analyte, concentrate the analyte, or the like. For example, the sample can be subjected to, ultrafiltration or elevated temperatures to remove interferents.

The aqueous medium may be solely water or may include from up to 50% volume percent of a cosolvent; usually less than 25%. Frequently cosolvents include low molecular weight alcohols which do not interfere in the assay to be performed. The pH for the medium will usually be in the range of about 5 to 11, more usually in the range of about 6 to 10.5, and preferably in the range of about 7 to 10. The pH value will usually be selected to maximize the extent and rate of the exchange of a hydrogen atom of the analyte with an isotope of hydrogen, usually a deuterium or tritium atom without causing excessive decomposition of the enzyme. Generally, the reversible oxidation reaction will be accelerated as the pH is increased and as the cofactor concentration is increased.

Various buffers may be used to achieve the desired pH and maintain the pH during the determination. Illustrative buffers include glycine, phosphate, carbonate, tris, barbital and the like. The particular buffer employed may depend on the assay to be performed. In an individual assay one or another buffer may be preferred. For example, when the analyte is a vicinal glycol such as occurs in saccharides, borate may interfere with the exchange by complexing with the analyte.

Moderate temperatures are normally employed for carrying out the assay and usually constant temperatures are maintained during the period of the measurement. Incubation temperatures will normally range from about 5° to 45° C., more usually from about 15° to 40° C. Temperatures during measurements will generally range from about 10° to 50° C., more usually from about 15° to 40° C.

The concentration of analyte that may be assayed will generally vary from below $10^{-16}$ to $10^{-5}$M, more usually from about $10^{-13}$ to $10^{-7}$M. Considerations such as the sensitivity of particular detection technique, the time desired to complete the assay, the cost of the reagents and the concentration of the analyte will normally determine the concentrations of the various reagents.

The concentration of the oxidant will usually be selected to optimize assay performance. In order to minimize the assay time, the oxidant concentration should preferably be at least as high as the $K_M$ of the enzyme with respect to the oxidant but lower concentrations may be used to minimize cost or avoid possible enzyme inhibition.

The concentration of the reducing agent will be similarly varied in order to optimize assay performance and must be present in sufficient concentration to provide a detectible signal following the exchange reaction. In order to minimize the assay time the reducing agent concentration should preferably be at least as high as the $K_M$ of the enzyme with respect to the reducing agent.

As for the enzyme, the greater the concentration of the enzyme the faster the reversible oxidation reaction. Usually the concentration of this reagent that is used will be determined by the cost of the enzyme and the desired time to carry out the exchange reaction. The enzyme concentration will usually be less than 10 mg/ml and may be as low as 10 ng/ml.

While the order of addition may be varied widely, there may be certain preferences. The simplest order of addition is to add all the materials simultaneously. Alternatively, the reagents can be combined sequentially. One or more incubation steps may be involved subsequent to each addition, longest generally ranging from about 30 seconds to 6 hours, more usually from about 60 seconds to 1 hour.

After all of the reagents have been combined, either simultaneously or sequentially, and after any appropriate incubation steps, the occurrence of exchange of a hydrogen atom of the analyte with an isotope of hydrogen, usually a deuterium or tritium atom is determined. The occurrence of exchange of a hydrogen atom of the analyte and an isotope of hydrogen is related to the presence or the amount of the analyte in the sample or assay medium tested. The non-occurrence of exchange of a hydrogen atom of the analyte and an isotope of hydrogen is related to the absence of the analyte in the sample assay medium tested.

Preferably, the step leading to the exchange reaction involves combining: (1) the sample, (2) an oxidant, (3) a reducing agent containing a deuterium or tritium atom, and (4) one or more enzymes which individually or together are capable of exchanging a hydrogen atom of the analyte with a deuterium or tritium atom of the reducing agent by catalyzing the reversible oxidation of the analyte.

The oxidant, reducing agent, enzyme(s) assay parameters, and format are selected as set forth above.

Determination of the amount of exchange will usually involve separating fractions of the sample or assay medium suspected of containing the analyte from other assay components, including the reducing agent, which contain an isotope of hydrogen. Such a separation can be accomplished by any suitable means such as multiphase extraction, chromatography (e.g. ion exchange chromatography, reverse-phase chromatography, gel exclusion chromatography, immunoaffinity chromatography, dye ligand chromatography, and the like), gel electrophoresis, isoelectric focusing, selective adsorption using a solid such a silica, alumina, zeolite, and the like. Preferably, such a separating step involves treating the sample or assay medium suspected of containing the isotopically labeled analyte with an agent capable of binding to the analyte. Preferably, the binding agent will be attached, or will be capable of being attached to a solid support or other means for separating it from other assay components, preferably from fractions of the sample or assay medium containing the reducing agent. Attachment to other means for separating may include attachment to magnetic or magnetizable particles, latex particles, precipitable polymers, specific binding pair members (e.g. avidin, biotin, antibody, hapten, or the like), polymerizable groups, or the like.

Once the desired separation has been performed, the occurrence of exchange of a hydrogen atom of the analyte with an isotope of hydrogen can be determined by use of any suitable means of detecting or measuring deuterium or tritium (e.g. mass spectrometry; detection of radioactivity, for example by photochemical detection, gas discharge or scintillation counting; nuclear magnetic resonance (NMR) or infrared spectroscopy (IR); and the like). Preferably, the means of detecting tritium will be by scintillation counting and the means of detecting deuterium will be by NMR.

Alternatively, the determining step can involve determining whether a hydrogen atom of the analyte has been exchanged with an isotope of hydrogen without separating the reducing agent which contains an isotopic atom from fractions of the sample or assay medium suspected of containing the analyte. Such a determination can be made by any of the methods of detecting the structural environment of hydrogen isotopes within a molecule such as mass spectrometry, nuclear magnetic resonance or infrared spectroscopy, and the like.

Another aspect of the invention relates to methods for determining the presence or the amount of an analyte having a primary or secondary hydroxy group in a sample suspected of containing the analyte. The method involves the steps of: (a) combining in an assay medium: (1) the sample, (2) an oxidant, (3) a reduced form of the oxidant that differs from the oxidant by at least the addition of a deuterium or tritium atom, and (4) an enzyme capable of catalyzing the exchange of hydrogen isotopes between the analyte and the reduced form of the oxidant; (b) incubating the assay medium for a sufficient time to permit exchange; and (c) determining the amount of deuterium or tritium incorporated into the analyte. The amount of exchange indicates the presence or amount of the analyte in the medium.

The oxidant, reduced form of the oxidant, enzyme, assay parameters and format are selected as set forth above.

Another aspect of the invention relates to improved methods for determining the presence or amount of an analyte capable of undergoing hydrogen exchange catalyzed by an oxidoreductase enzyme in a sample suspected of containing the analyte. The improvement of this aspect of the invention involves the steps of: (1) combining in an assay medium: (a) the sample, (b) a hydrogen isotope-enriched compound capable of transferring the hydrogen isotope into the analyte as a result of the action of the enzyme on the analyte; and (2) detecting the analyte having the hydrogen isotope.

The detecting step can involve separating the compound from the analyte. In one embodiment the separating step involves treating the medium with an agent capable of binding the compound. In one such embodiment the agent is attached to, or is capable of being attached to, a solid support or other means for separating it from the analyte. Alternatively, the separating step can involve treating the medium with an agent capable of binding the analyte. In one such embodiment the agent is attached to, or is capable of being attached to, a solid support or other means for separating it from the compound Alternatively, the detecting step can be accomplished without separating the compound from the medium, as for example, by use of spectroscopic means for detecting the presence or amount of analyte having a hydrogen atom exchanged with an isotope of hydrogen, usually a deuterium or tritium atom.

The oxidant, reducing agent, enzyme(s), assay parameters and format, are selected as set forth above.

To further illustrate, but not limit, the scope of the invention, assays using the enzymes of Table 1 will be described.

Homoserine and aspartic-β-semialdehyde are determined using homoserine dehydrogenase from Baker's Yeast (Anheuser-Busch) obtained by the procedure of Black, S. "Methods in Enzymology", vol. V, page 820 (Academic Press, New York, 1962), pages 824–827 of which are incorporated herein by reference. The assay is specific for the L-isomers of homoserine and aspartic-β-semialdehyde, the D-isomers of which will not interfere with the assay results. Other non-interfering substances will include 3-aminopropanol, γ-hydroxybutyrate, acetaldehyde, DL-threonine, DL-serine, and DL-homocysteine. DL-glutamic γ-semialdehyde will react at 1% of the rate of aspartic-β-semialdehyde.

D-lactate and pyruvate in plasma are determined using D-lactate dehydrogenase from *Lactobacillus leichmannii* (Sigma or Boehringer-Mannheim biochemicals) obtained by the procedure of Brandt, R. B. "Methods in Enzymology", vol. 89, page 35 (Academic Press, New York, 1982), pages 35–40 of which are incorporated herein by reference. The assay will detect D-lactate concentrations in plasma from 0.006 to 1.2 mM and at higher concentrations in food or microbiological samples. If the enzyme is from *Lactobacillus plantarum* obtained according to Dennis, D.; Kaplan, N. O. *J. Bio. Chem.* 1960, 235, 810, the relevant portion of which is incorporated herein by reference, then L-lactate, 2-hydroxy-D-butyrate, D-caproate, D-isocaproate, Disovalerate, phenylacetate and 2-oxoglutarate will not interfere with the assay results; 2-oxobutyrate will react at a rate 25% that of pyruvate; and AND(P) will not replace NAD.

D-mannonate and D-fructuronate are determined using fructuronate reductase from Escheria coli K-12 strain S 3000 (Hfr H) obtained by the procedure of Portalier, R.; Stoeber, F. "Methods in Enzymology", vol. 89, page 210 (Academic Press, New York, 1982), pages 210–218 of which are incorporated herein by reference. D-glucuronate, D-galacturonate, D-mannuronate, D-fructose, D-tagatose, D-mannose, D-glucose, D-galactose, D-sorbose, D-arabinose, L-arabinose, D-ribose, L-lyxose, D-xylose, L-xylose, D-ribulose, D-manno-heptose, and D-altro-heptulose will not interfere with assay results. AND(P) will not substitute for AND. D-tagaturonate and D-altronate are 20% as active as D-fructuronate and D-mannonate, respectively.

Estradiol-17β and estrone are determined using soluble 17β-hydroxysteroid dehydrogenase from human term placenta obtained by the procedure of Jarabak, J. "Methods in Enzymology", vol. 15, page 746 (Academic Press, New York, 1982), pages 746–752 of which are incorporated herein by reference. 17α-estradiol and 16β-estradiol will not interfere with the assay results. Progesterone and its 20α-hydroxy derivative will react at a rate one-fiftieth that of estrone.

10-hydroxydecanoate and 10-oxodecanoate are determined using ω-hydroxydecanoate dehydrogenase from rabbit liver obtained by the procedure of Kamei, S., Wakabayashi, K.; Shimazono, N. *J. Biochem. (Tokvo)* 1964, 56, 72, the relevant portion of which is incorporated herein by reference. 6-hydroxy-caproate, 10-hydroxystearate, 3-hydroxybutyrate, ethanol, ethanolamine, choline, serine, threonine, pantothenate, mevalonate and pyridoxine will not interfere with assay results. 11-hydroxy undecanoate (100), 10-hydroxycaproate (0.90) and 9-hydroxypelargonate (0.27) will all react at various rates. AND(P) will be inactive in the place of AND. The enzyme obtained will be contaminated to some degree with L-lactate dehydrogenase (I.U.B. 1.1.1.27).

Glycerol and D-glyceraldehyde are determined using glycerol dehydrogenase from New Zealand white rabbit skeletal muscle obtained by the procedure of Flynn, T. G.; Cromlish, J. A. "Methods in Enzymology", vol. 89, page 237 (Academic Press, New York, 1982), pages 237–242 of which are incorporated herein by reference. Two enzymes (GDH$_1$ and GDH$_2$) will be isolated. Both will have a broad substrate specificity so that D-glyceraldehyde, L-glyceraldehyde, glycolaldehyde, methylglyoxal, propionaldehyde, butyraldehyde, valeraldehyde, D-erythrose, D-xylose, D-glucose, and p-nitrobenzaldehyde will all be determined. GDH$_1$ is distinguished from GDH$_2$ in its greater affinity for D-glucose ($K_M$ will be about 156 mM for GDH$_1$ and 527 mM for GDH$_2$).

11α,15-dihydroxy-9-oxoprost-13-enoate and 11α-hydroxy-9, 15-dioxoprost-13-enoate are determined using 15-hydroxyprostaglandin dehydrogenase from pig lung obtained by the procedure of Anggard, E.; Samuelsson, B. "Methods in Enzymology", vol. 14, page 215 (Academic Press, New York, 1969), pages 215–219 of which are incorporated herein by reference. The assay will detect most 15-hydroxy or 15-oxo-prostaglandins except those containing the dienone chromophore such as prostaglandin B compounds and their 19-hydroxylated derivatives. NAD(P) will not replace NAD.

Cortisol and 21-dehydrocortisol are determined using AND dependent 21-hydroxysteroid dehydrogenase from sheep liver obtained by the procedure of Monder, C.; Furfine, C. S. "Methods in Enzymology", vol. 15, page 667 (Academic Press, New York, 1969), pages 667–675 of which are incorporated herein by reference. 21-hydroxy-derivatives of cortisol, cortisone, corticosterone, 11-deoxycortisol, Δ$^1$-cortisone, Δ$^1$-cortisol, 11-deoxycorticosterone, and 9α-fluorocortisol will all be assayed using this enzyme. Cortisol, cortisone, 11-deoxycorticosterone, aldosterone, isoandrosterone, testosterone, estrone, acetaldehyde, DL-glyceraldehyde, p-tolualdehyde, o-anisaldehyde, salicylaldehyde, benzaldehyde, methyl glyoxal, and glyoxal will not interfere in the assay results. AND(P) will not replace NAD.

Another aspect of the invention relates to kits which include in packaged combination reagents and materials used in the assay methods of the invention.

To enhance the versatility of the subject invention, the reagents can be provided in packaged combination, in the same or separate containers, so that the ratio of the reagents provides for substantial optimization of the methods and assays. The reagents may each be in separate containers or various reagents can be combined in one or more containers depending on the cross-reactivity and stability of the reagents. The kit comprises as one reagent an enzyme in accordance with the invention capable of catalyzing the reversible oxidation of the analyte, and as a second reagent a reducing agent in accordance with the invention containing an isotope of hydrogen, usually a deuterium or tritium atom. The kit can further comprise as a third reagent an oxidant in accordance with the invention.

The kit can further include other separately packaged reagents for conducting an assay in accordance with the invention such as supports, ancillary reagents, sample pretreatment reagents, and so forth. A support can be a porous or non-porous water insoluble material. The support can be hydrophilic or capable of being rendered hydrophilic and includes inorganic powders, natural polymeric materials; synthetic or modified naturally occurring polymers, such as plastics; glass; ceramics; metals and the like.

EXAMPLES

The invention is further demonstrated by the following illustrative and not limiting examples. Parts and percentages used herein are by weight unless otherwise indicated. Temperatures are in degrees centigrade (° C.).

EXAMPLE 1

PURIFICATION OF ENZYMES

A. D-ARABINITOL DEHYDROGENASE FROM *CANDIDA TROPICALIS*

Centrifugation and other protein purification steps were performed at 4° C. unless otherwise noted. Four liters of *Candida tropicalis* cells were grown in Yeast Nitrogen Base (Difco) supplemented with 0.5% (w/v) D-arabinitol on a gyrotary shaker at room temperature. The cells were harvested by centrifugation after they reached late log phase in their growth cycle ($OD_{660} > 5.0$). The cells were then washed with distilled water, repelleted and the wet weight of the cell pellets was determined. The pellets were resuspended in 0.1 M $NaH_2PO_4$, $10^{-7}$ M pepstatin A, 1 mM phenylmethylsulfonyl fluoride, pH 7.0 with NaOH at room temperature, using 2 mL of the above buffer per gram of wet weight cells. Acid-washed glass beads (0.45-0.55 mm) were added to the resuspended pellets using two grams of beads for each gram of wet weight cells. The cells were then disrupted in a Braun MSK Cell Homogenizer for 5 min while being cooled with liquid nitrogen. The disrupted cells were removed from the glass beads and were spun at 5,000 × g for 5 min to pellet cell wall material. The supernatant was removed and spun at 100,000 × g at 4° C. for 1 hr in an ultracentrifuge. The resulting supernatant was removed and its volume and protein concentration was determined. For every gram of protein, 90 mg of protamine sulfate was added dropwise from a 2% (w/v) stock over 5 min while stirring on ice. After equilibrating the solution by stirring for an additional 5 min on ice, the nucleic acid-protein precipitate was removed by centrifugation at 30,000 × g for 15 min. The resulting supernatant was brought up to 40% saturation with ammonium sulfate crystals, which were added over a period of 20 min while stirring the solution on ice. After equilibrating the solution by stirring for an additional 30 min on ice, the protein precipitate was recovered by spinning the solution at 100,000 × g for 15 min. The resulting pellet was resuspended in running buffer (50 mM $NaH_2PO_4$, 0.5 M NaCl, 5 mM $MgCl_2$, $10^{-7}$ M pepstatin A, pH 7.0 with NaOH at room temperature) using 1/20th the volume of the 100,000 × g supernatant. The protein solution was then loaded on a reactive yellow 86 dye ligand column (1 cm × 3.5 cm) and the column was washed with 5 column volumes of running buffer. It should be noted that other dye ligand columns can be used in this step of the procedure, when lesser purification factor can be tolerated. Such dye ligands include by way of illustration and not limitation reactive blue 4, reactive red 120, reactive blue 2, reactive green 5, reactive blue 72, and reactive yellow 3. The D-arabinitol dehydrogenase was eluted by washing the column with 3 column volumes of running buffer supplemented with 1 mM NADH. The eluted protein was concentrated using a Centricon 30 microconcentrator device (Amicon) to a final concentration of at least 1 mg/mL. The D-arabinitol dehydrogenase was stored at −80° C. The average yield of D-arabinitol dehydrogenase was 1.0-1.5 mg while purity was greater than 90% as judged by sodium dodecysulfate (SDS)-polyacrylamide gel electrophoresis. Table 2 summarizes the protein purification results.

TABLE 2

*C. TROPICALIS* ATCC 750 PROTEIN PURIFICATION TABLE

| SAMPLE | VOLUME (mL) | TOTAL PROTEIN (mg) | TOTAL ACTIVITY* (μmoles NADH formed per min) | SPECIFIC ACTIVITY (Activity per mg protein) | PURIFICATION FACTOR (P.F.) | YIELD (%) |
|---|---|---|---|---|---|---|
| 100,000 × g | 55 | 1661 | 422.4 | 0.254 | 1.00 | 100 |
| Protamine SO4 | 60 | 1888 | 446.4 | 0.236 | 0.93 | 100 |
| (NH4)2SO4 | 3 | 110.7 | 225.6 | 2.038 | 8.62 | 53.4 |
| Y-86 Column | 0.162 | 1.2 | 243.7 | 203.0 | 99.62 overall P.F. 799.2 | 58.0 |

*Activity was determined in 1 mL of 1.5 mM NAD, 50 mM D-arabinitol in 50 mL 3-(cyclohexylamino)-2-hydroxy-1-propanesulfonic acid (CAPSO), pH 9.5, 100 mM NaCl, 5 mM Mgcl2 at 25° C. The production of NADH was monitored by an increase in absorbance at 340 nm over 1 min starting 15 sec after the addition of enzyme.

B. D-ARABINITOL DEHYDROGENASE AND POLYOL DEHYDROGENASE FROM *C. SHEHATAE*

The purification of D-arabinitol dehydrogenase from *C. shehatae* was similar to the purification of D-arabinitol dehydrogenase from *C. tropicalis* with some exceptions. The cells disrupted in Braun MSK Cell Homogenizer were removed from the glass beads and spun at 30,000 × g for 15 minutes to pellet cell wall material. In addition, 60% saturation with ammonium sulfate was used instead of 40%, to precipitate the protein. This allowed the precipitation of both the D-arabinitol dehydrogenase and the polyol dehydrogenase. The D-arabinitol dehydrogenase was purified over a reactive yellow 86 dye ligand column as described in Example 1. The polyol dehydrogenase from this same strain was purified by running the flow-through from the reactive yellow 86 dye ligand column through a reactive blue 2 dye ligand column (1.0 cm × 6.0 cm). The polyol dehydrogenase was then eluted by washing the column with 3 column volumes of running buffer supplemented with 10 mM NAD.

C. D-ARABINITOL DEHYDROGENASE FROM *AEROBACTER AEROGENES*

D-arabinitol dehydrogenase from *Aerobacter aerogenes* (lyophilized cells Type 1, Sigma) was purified as described in Neuberger, et al., in *Biochem. J.*, 183 (1979) 31–42.

EXAMPLE 2

PREPARATION OF MONOCLONAL ANTIBODIES AGAINST *CANDIDA TROPICALIS* D-ARABINITOL DEHYDROGENASE

A. GENERAL METHODS

The standard hybridoma procedures used have been described in detail (Kohler, G.; Milstein, C. *Nature* 1975, 256, 495–7; Hurrell, J. G. R. "Monoclonal Hybridoma Antibodies: Techniques and Applications", CRC Press, 1982, Boca Raton, Fla. 33431).

B. IMMUNIZATION

Balb/C mice (Charles River Laboratories) were immunized with 50 ug of immunogen by either intraperitoneal or subcutaneous injection. The immunogen was prepared by diluting purified D-arabinitol dehydrogenase from *Candida topicalis* (see Example 1) into Hanks Balanced Saline Solution (HBSS) at a concentration of 500 µg/2.0 mL. The antigen was then added to an adjuvant mixture of monophosphoryl lipid A and trehalose dimycolate in 2% squalene (RIBI Immunochemical Research Inc.) and used for injections. Mice were boosted twice with 50 µg of immunogen. A final intravenous injection of 200 ug *C. tropicalis* D-arabinitol dehydrogenase in HBSS was performed prior to fusion.

C. CELL FUSION

Spleen cells were harvested from the immunized mice and fused with P3 X63-AG8.653 myeloma cells (ATCC #CRL 1580) using polyethylene glycol. The cells were resuspended in HAT (0.mM hypoxanthine, 0.016 mM thymidine and 0.4 µM aminopterin, Sigma) supplemented media and distributed into 96-well microtiter plates. Four days later cells were fed by replacing half the HAT supplemented media.

D. HYBRIDOMA SCREENING

Hybridomas were screened for antibodies specific for *C. tropicalis* D-arabinitol dehydrogenase by a reverse ELISA method. Microtiter EIA plates (Costar #3595) were coated with rabbit anti-mouse IGA, A, M, heavy and light chains (Zymed) at a 1:100 dilution in PBS (0.01 M NaHPO$_4$, 0.01 M NaH$_2$PO$_4$, 0.015 M NaCl, 0.001% NaN$_3$, adjusted to pH 7.2). 100 ul of the above solution was added per well and incubated either at 37° for at least one hour or at 4° overnight. Any unbound sites on the plate were blocked with 1% (v/v) normal sheep serum (NSS, Sigma) in PBS (200 ul/well). After blotting off the NSS, 50 ul of hybridoma culture supernatant was added per well. The plates were incubated at 25° for one hour. The plates were then washed four times with ELISA Wash Buffer (0.05% (v/v) Tween-20 in PBS). Excess wash buffer was blotted from the plate and a 2 ug/mL solution of D-arabinitol dehydrogenase in PBT (0.2% (w/v) bovine serum albumin and 0.1% (v/v) Tween-20 in PBS) was added to the plate at 100 ul/well. The EIA plate was incubated for one hour at 25°. The plates were then washed four times with ELISA Wash Buffer and excess buffer was blotted from the plate. The plates were then developed with a substrate solution containing 50 mM D-arabinitol (Aldrich) and 1.5 mM AND+ $^{in}$ 50 mM CAPSO, 100 mM NaCl, 5 mM MgCl$_2$ adjusted to pH 9.5. The plates were incubated at 37° for 30 minutes and the NADH product was measured at 340 nm. Alternatively, the production of NADH was coupled with the reduction of p-iodonitrotetrazolium violet (INT, Sigma) through the enzyme diaphorase (Sigma). Diaphorase (0.534 IU/mL, final concentration) and INT (0.074 mM, final concentration) were added to the above reaction mixture. The reaction was incubated as above and the production of reduced INT was monitored at 492 nm. Wells with readings at least three times higher than the background were considered positive Cells from ELISA positive wells were subcloned until stable monoclonal antibody secretion was achieved During the subcloning, ELISA screens were also done substituting *C. shehatae* D-arabinitol dehydrogenase for the *C. tropicalis* enzyme.

E. ANTIBODY PRODUCTION IN ASCITES

To scale up monoclonal antibody production in ascites, mice were primed by an intraperitoneal injection of Incomplete Freund's Adjuvant to facilitate tumor growth 2 to 7 days prior to passage of cells. Cells were grown up in a T-75 flask, to a final density of about 18 × 10$^6$ cells in 50 mL, centrifuged, and then resuspended in 2 mL of Dulbecco's Modified Eagle Medium (Gibco) with 10% FBS, 10% NCTC-135 (Gibco), 1 mM oxaloacetic acid (Sigma), 1 mM sodium pyruvate (Gibco), 4 mM L-glutamine (Sigma), 50 ug/mL gentamicin (Gibco), 10 ug/mL insulin (Sigma), 20 mM Hepes (Sigma). Each mouse received a 0.5 mL intraperitoneal injection of approximately 4–5 × 10$^6$ cells. Ascites tumors usually developed within a week or two. The ascites fluid containing a high concentration of antibody was drained from the peritoneal cavity using a hypodermic needle. The fluid was allowed to clot at room temperature and then centrifuged at 1500 rpm in a Beckman Model TJ-6 Centrifuge for 30 minutes. The antibody containing fluid was poured off and stored at 4°.

EXAMPLE 3

ELISA BINDING OF MONOCLONAL ANTIBODIES TO DIFFERENT D-ARABINITOL DEHYDROGENASES

Monoclonal antibodies produced against *C. tropicalis* D-arabinitol dehydrogenase were screened for binding to D-arabinitol specific dehydrogenases purified from C. tropicalis and from C. shehatae by the reverse ELISA method described above. These monoclonal antibodies were also screened for binding to polyol dehydrogenases that could utilize other sugar substrates in addition to D-arabinitol. A C. shehatae polyol dehydrogenase that could utilize D-arabinitol, D-sorbitol, xylitol and D-mannitol was tested. Also tested was D-arabinitol dehydrogenase from Aerobacter aerogenes, an enzyme that uses either D-arabinitol or D-mannitol as a substrate.

The reverse ELISA screening was as above except a 1:100 dilution of ascites in PBT (100 uL/well) was used instead of culture supernatant. In addition, the purified D-arabinitol dehydrogenases from each strain were diluted to 0.2 IU/mL (where an international unit is the amount of NADH produced/min). As a control, the D-arabinitol dehydrogenase activity was confirmed for each activity assay as follows: 10 uL of unbound D-arabinitol was removed from ELISA wells and enzyme activity was checked with the developing reagents as described above. For a negative antibody control, Chlamydia trachomatis-immunized mouse sera diluted 1:100 in PBT was used.

Results are summarized in Table 3. Each monoclonal antibody was analyzed in duplicate (DUP) with each of the four enzymes. Blanks were run by repeating the above experiments in the absence of the monoclonal antibodies and blank readings were subtracted from the DUP values. The average of the DUP values is presented in Table 3. The results show that the monoclonal antibodies produced against C. tropicalis D-arabinitol dehydrogenase bind the D-arabinitol-specific dehydrogenases from both C. tropicalis and C. shehatae, as evidenced by ELISA readings that are elevated relative to those observed in the absence of antibody (blank) or with the Chlamydia antibody. In contrast, relatively little, if any, binding is seen with the polyol dehydrogenases purified from C. shehatae and from A. aerogenes as evidenced by the fact that these readings are not significantly higher than those observed in the blank or with the Chlamydia antibody. These results demonstrate that the monoclonal antibodies bind only D-arabinitol specific dehydrogenases and do not bind to less specific dehydrogenases that utilize either D-arabinitol or other sugar alcohols as substrates.

TABLE 3

ELISA BINDING OF POLYOL DEHYDROGENASES TO MONOCLONAL ANTIBODIES SPECIFIC FOR C. TROPICALIS D-ARABINITOL DEHYDROGENASE

| Antibody | CTDADH[1] | CDDADH[2] | CSPDH[3] | AADADH[4] |
|---|---|---|---|---|
| 3D6 | 0.201 | 0.146 | 0.009 | 0.004 |
| 5e11 | 0.237 | 0.169 | 0.008 | 0.004 |
| 1B9 | 0.171 | 0.049 | 0.007 | 0.003 |
| 5F3 | 0.186 | 0.079 | 0.006 | 0.002 |
| 6B3 | 0.265 | 0.060 | 0.004 | −0.002 |
| 1H4 | 0.337 | 0.043 | −0.002 | −0.001 |
| chlamydia | 0.007 | 0.005 | 0.003 | 0.010 |

[1]CTDADH = C. tropicalis D-arabinitol dehydrogenase
[2]CSPADH = C. shehatae D-arabinitol dehydrogenase
[3]CSPHD = C. shehatae polyol dehydrogenase
[4]AADADH = A. aerogenes D-arabinitol dehydrogenase

EXAMPLE 4

A RADIOISOTOPIC EXCHANGE ASSAY FOR D-ARABINITOL IN HUMAN SERUM

Tritium Exchange Assay Protocol

Assay incubation solutions (vol.=0.1 mL) contained 0.05 mL ultrafiltered human serum, 0.2 mmol/L unlabeled NAD+, 0.015 mmol/L (0.62 Ci/mmol) [4(S)−$^3$H]NADH, 2 mg/mL BSA, 0.2 mmol/L DTT, 4 mmol/L Mg$^{2+}$, 40 mmol/L Tris (pH 9.2), and 0.35 IU C. tropicalis D-arabinitol dehydrogenase. Incubation was for 2 hr. at room temperature to promote the D-arabinitol dehydrogenase-catalyzed exchange of tritium from [4(S)−$^3$H]NADH into D-arabinitol. After incubation, the sample was diluted with 0.9 mL distilled water and applied to a 2 mL column of AG 2-X8 (Bio Rad, Cat. No. 731-6247) preequilibrated in the −OH form. The column was eluted with 6 mL distilled water and the eluate was collected, diluted 1:1 (v/v) with 250 mmol/L NH$_4$OAc (pH 8.8), and applied to a 1 mL column of phenylboronate (Pierce, Cat. No. 20368) preequilibrated with the NH$_4$OAc buffer. The column was washed with 10 mL of 250 mmol/L NH$_4$OAc (pH 8.8) and subsequently eluted with 4 mL of 0.1 formic acid. The formic acid i0 eluate was analyzed for tritium by scintillation spectrometry.

Calibration Curve For the Tritium Exchange Assay

Results from a series of assays of a pool of normal human serum into which various amounts of D-arabinitol had been added are illustrated in Table 4. A plot of tritium recovered (Y-axis) vs. the amount of D-arabinitol added (X-axis) yields the calibration curve for the assay. The absolute value of the X-intercept of the curve is a measure of the sum of endogenous D-arabinitol and D-ribulose present in the serum pool. The endogenous serum concentration of D-ribulose can be obtained by carrying out the assay under similar conditions but in the absence of AND+ and determining tritium incorporation into D-arabinitol. The calibration curve is linear (r=0.990) and the observed D-arabinitol concentrations in supplemented samples differed from the expected amounts (endogenous + amount added) by no more than 0.42 μmol/L or 7.9%.

TABLE 4

CALIBRATION CURVE FOR THE TRITIUM EXCHANGE ASSAY

| Assay No. | D-Arabinitol Added (μmol/L) | Tritium Recovered (cpm × 0.001) |
|---|---|---|
| 1 | 0 | 25.5 |
| 2 | 2 | 45.3 |
| 3 | 4 | 62.8 |
| 4 | 6 | 72.9 |
| 5 | 8 | 90.8 |

$y = 27.82 + 7.91X$
$r^2 = 0.990$

The patents and patent applications referred to in the above description are each incorporated herein by reference in their entirety.

Although the foregoing invention has been described in some detail by way of illustration and example for the purposes of clarity and understanding, it will be obvious that certain changes or modifications may be practiced within the scope of the appended claims.

What is claimed is:

1. A method for determining the presence or amount of an analyte wherein an enzyme catalyzes reversible oxidation of said analyte with exchange of a hydrogen atom with an isotope of hydrogen in a sample suspected of containing said analyte, which method comprises:

(1) treating said sample to enzymatically exchange said hydrogen atom with a deuterium or tritium atom if said analyte is present; and (2) determining whether said hydrogen atom has been exchanged with said deuterium or tritium atom, the occurrence of said exchange indicating the presence or amount of said analyte in said sample.

2. The method of claim 1 wherein said treating comprises combining:
(1) said sample,
(2) an oxidant,
(3) a reducing agent containing said deuterium or tritium atom, and
(4) one or more enzymes which individually or together exchange said hydrogen atom with said deuterium or tritium atom of said reducing agent by catalyzing the reversible oxidation of said analyte.

3. The method of claim 2 wherein a single enzyme is employed.

4. The method of claim 2 wherein said determining comprises separating said reducing agent from said sample suspected of containing said analyte.

5. The method of claim 4 wherein said separating comprises treating said sample with an agent which specifically binds said analyte.

6. The method of claim 4 wherein said determining further comprises detecting or measuring the amount of radioactivity of said sample.

7. The method of claim 2 wherein said determining comprises determining whether said hydrogen atom has been exchanged with said deuterium or tritium atom without separating said reducing agent from said sample suspected of containing said analyte.

8. The method of claim 1 wherein said determining comprises detecting said exchange by spectroscopic means.

9. The method of claim 1 wherein said treating comprises combining:
(1) said sample,
(2) an oxidant,
(3) a reduced form of said oxidant that differs from said oxidant by at least the addition of a deuterium or tritium atom, and
(4) an enzyme which catalyzes the exchange of hydrogen isotopes between said analyte and said reduced form of said oxidant.

10. A method for determining the presence or the amount of an analyte having a primary or secondary hydroxy group in a sample suspected of containing said analyte, which comprises:
(a) combining in an assay medium:
(1) said sample,
(2) an oxidant,
(3) a reduced form of said oxidant that differs from said oxidant by at least the addition of a deuterium or tritium atom, and
(4) an enzyme which catalyzes the exchange of hydrogen isotopes between said analyte and said reduced form of said oxidant;
(b) incubating said assay medium for a sufficient time to permit said exchange; and
(c) determining the amount of said deuterium or tritium atom incorporated into said analyte.

11. The method of claim 10 wherein said analyte is a saccharide.

12. The method of claim 11 wherein said saccharide is d-arabinitol.

13. The method of claim 10 wherein said enzyme is selected from the group consisting of AND dependent dehydrogenases, and NADP dependent dehydrogenases.

14. A method of claim 10 wherein said enzyme is d-arabinitol dehydrogenase.

15. The method of claim 10 wherein said reduced form of said oxidant is selected from the group consisting of deuterated or tritiated NADH, NADPH and FMNH.

16. The method of claim 10 wherein said reduced form of said oxidant is deuterated or tritiated NADH.

17. The method of claim 10 wherein said oxidant is selected from the group consisting of NAD, NADP and FMN.

18. The method of claim 10 wherein said oxidant is NAD.

19. The method of claim 10 wherein said sample comprises analyte separated from a natural sample.

20. The method of claim 19 wherein an agent which binds said analyte is used for said separation.

21. The method of claim 10 wherein said analyte and said reduced form of said oxidant are separated prior to said determining.

22. The method of claim 21 wherein an agent which binds said analyte is used for said separation.

23. The method of claim 21 wherein an agent which binds said oxidant is used for said separation.

24. In a method for determining the presence or amount of an analyte which undergoes hydrogen exchange catalyzed by an oxidoreductase enzyme in a sample suspected of containing said analyte, the improvement which comprises:
(1) combining in a medium:
(a) said sample,
(b) said enzyme, and
(c) a hydrogen isotope-enriched compound which transfers said hydrogen isotope into said analyte as a result of the action of said enzyme of said analyte; and
(2) detecting said analyte having said hydrogen isotope.

25. The method of claim 24 wherein said hydrogen isotope-enriched compound is separated from said analyte prior to said detecting.

26. The method of claim 25 wherein said compound is separated by contacting said medium with an agent which binds said compound.

27. The method of claim 26 wherein said agent is selected from the group consisting of an antibody and a lectin.

28. The method of claim 25 wherein said compound is separated by contacting said medium with an agent which binds said analyte.

29. The method of claim 28 wherein said agent is selected from the group consisting of an antibody, an aryl boronate, and a lectin.

30. The method of claim 24 wherein said detecting comprises a spectroscopic measurement.

31. The method of claim 24 wherein said sample comprises analyte separated from a test solution by means of an agent which binds said analyte.

32. The method of claim 24 wherein said analyte comprises a primary or secondary alcohol.

33. The method of claim 24 wherein said analyte is a saccharide.

34. The method of claim 33 wherein said saccharide is d-arabinitol.

35. The method of claim 24 wherein said enzyme is selected from the group consisting of AND dependent dehydrogenases, and NADP dependent dehydrogenases.

36. A method of claim 24 wherein said enzyme is d-arabinitol dehydrogenase.

37. The method of claim 24 wherein said compound is selected from the group consisting of deuterated or tritiated NADH, NADPH and FMNH.

38. The method of claim 24 wherein said compound is deuterated or tritiated NADH.

39. A kit for conducting a method for determining the presence or amount of an analyte wherein an enzyme catalyzes reversible oxidation of said analyte with exchange of a hydrogen atom with an isotope of hydrogen in a sample suspected of containing said analyte, said kit comprising in packaged combination:
(1) a reducing agent containing a deuterium or tritium atom, and
(2) one or more enzymes which individually or together exchange said hydrogen atom with said deuterium or tritium atom of said reducing agent by catalyzing the reversible oxidation of said analyte.

40. The kit of claim 39 wherein a single enzyme is employed.

41. The kit of claim 40 wherein said enzyme is an oxidoreductase.

42. The kit of claim 41 wherein said oxidoreductase is selected from the group consisting of NAD dependent dehydrogenases, and NADP dependent dehydrogenases.

43. A kit of claim 41 wherein said oxidoreductase is d-arabinitol dehydrogenase.

44. The kit of claim 39 wherein said reducing agent is selected from the group consisting of deuterated or tritiated NADH, NADPH and FMNH.

45. The kit of claim 39 wherein said reducing agent is deuterated or tritiated NADH.

46. The kit of claim 39 which further comprises in packaged combination an oxidant.

47. The kit of claim 46 wherein said oxidant is selected from the group consisting of NAD, NADP and FMN.

48. The kit of claim 46 wherein said oxidant is NAD.

49. The kit of claim 39 which further comprises in packaged combination an agent that binds said analyte or said reducing agent.

50. The kit of claim 49 wherein said agent is selected from the group consisting of an antibody, lectin, and an aryl boronate.

* * * * *